United States Patent [19]

Kuhn et al.

[11] Patent Number: 5,180,734

[45] Date of Patent: Jan. 19, 1993

[54] INSECTICIDAL AND ACARICIDAL DIARYLPYRROLECARBONITRILE AND DIARYLNITROPYRROLE COMPOUNDS

[75] Inventors: David G. Kuhn, Newtown, Pa.; Joseph A. Furch, Lawrenceville; Victor M. Kamhi, Hamilton Sq., both of N.J.

[73] Assignee: American Cyanamid Company, Stamford, Conn.

[21] Appl. No.: 621,162

[22] Filed: Nov. 30, 1990

[51] Int. Cl.⁵ .............................. A01N 43/36
[52] U.S. Cl. .......................... 514/426; 548/558; 548/561
[58] Field of Search ............... 548/558, 561; 514/426

[56] References Cited

U.S. PATENT DOCUMENTS 4,798,901  1/1989  Tessier et al. ............ 548/562
5,010,098  4/1991  Brown et al. ............. 514/426

Primary Examiner—Marianne M. Cintins
Assistant Examiner—John Peabody
Attorney, Agent, or Firm—John W. Hogan, Jr.

[57] ABSTRACT

This invention relates to new diarylpyrrolecarbonitrile and new diarylnitropyrrole compounds. It also relates to the use of said compounds as insecticidal and acaricidal agents and to a method of protecting plants, particularly crop plants, from attack by insects and acarina by application of a new diarylpyrrolecarbonitrile or diarylnitropyrrole to said plants or to the locus in which they are growing.

7 Claims, No Drawings

INSECTICIDAL AND ACARICIDAL DIARYLPYRROLECARBONITRILE AND DIARYLNITROPYRROLE COMPOUNDS

BACKGROUND OF THE INVENTION

Synthetic pyrroles are described in the literature and reported to be effective as antibacterial and fungicidal agents.

S. Inouge et al., in U.S. Pat. No. 4,563,472, disclose a variety of iodoallyl and iodopropargyl tetrazoles, nitroimidazoles and nitropyrrole derivatives that exhibit some antimicrobial and antifungal activity. The patentees exemplify the antibacterial and antifungal activity of their compounds, but make no reference to any insecticidal, acaricidal or molluscicidal activity observed or indicated for such compounds or derivatives thereof.

M. Koyama et al describe the preparation of several nitropyrroles including: mono, di and trichloronitropyrroles in an article published in The Journal of Antibiotics 34, 1569-1576 (1981). The reported compounds were evaluated as antibacterial agents and the biological activities of the synthesized compounds is reported in said paper.

D. M. Bailey in U.S. Pat. No. 3,985,539 describes the preparation of 4,5-dihalopyrrole-2-carbonitriles and the use thereof as terrestrial and aquatic herbicides. The patentee also indicates that the patented compounds exhibit some activity as antibacterial and antifungal agents. However, insecticidal, acaricidal and molluscicidal activity for the halopyrrole carbonitriles is not disclosed, described or suggested.

It is also noted that certain nitropyrroles, dinitropyrroles, cyanonitropyrroles, and cyanodinitropyrroles, which include N-substitution by methyl, propyl, or hydroxyethyl groups, have been examined as radiosensitizers by Raleigh et al in the British Journal of Cancer, Suppl. 37 (1978), but the abstract is totally devoid of any reference to other types of activity for the disclosed compounds.

The Fisons European Patent Application Publication Number 0,300,688, application number 88306464.4 filed Jul. 7, 1988 discloses a variety of pyrrole derivatives as cardiotonic agents useful for the treatment of hypotonic circulatory conditions, elevated blood sugar, psychiatric illness, depression and like conditions. No insecticidal or acaricidal is alleged for the disclosed compounds.

SUMMARY OF THE INVENTION

This invention relates to new diarylpyrrolecarbonitrile or diarylnitropyrrole compounds illustrated by the structures of formulas I and II:

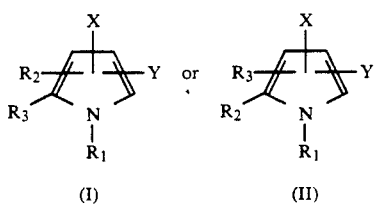

wherein
$R_1$ is H;
  $C_1-C_4$ alkyl or $C_2-C_4$ monohaloalkyl, each optionally substituted with from one to three additional halogen atoms, one cyano, one hydroxy, one unsubstituted benzoyl, one or two $C_1-C_4$ alkoxy groups each optionally substituted with one to three halogen atoms, one $C_1-C_4$ alkylthio, one $C_1-C_4$ carbalkoxy, one $C_1-C_6$ alkylcarbonyloxy, one $C_2-C_6$ alkenylcarbonyloxy, one benzenecarbonyloxy, or chloro, dichloro, or methylsubstituted-benzenecarbonyloxy, one phenyl optionally substituted with $C_1-C_3$ alkoxy or with one to three halogen atoms, one phenoxy optionally substituted with one to three halogen atoms, or one benzyloxy optionally substituted with one halogen substituent;
  $C_3-C_4$ alkenyl optionally substituted with one to three halogen atoms;
  cyano;
  $C_3-C_4$ alkynyl optionally substituted with one halogen atom;
  di-($C_1-C_4$ alkyl)aminocarbonyl; or
  $C_3-C_6$ polymethyleneiminocarbonyl;
$R_2$ is CN or $NO_2$;
$R_3$ is halogen or $CF_3$;
X and Y are each independently phenyl optionally substituted with one or two halogen, CN, $NO_2$, $C_1-C_4$ alkyl, $C_1-C_4$ alkoxy, $CF_3$ or $OCF_2R_4$ groups; and
R is H, F, $CHF_2$, $CHCl_2$ or $CF_3$;
with the proviso that when X and Y are attached to the carbons in the 3- and 4-positions of the pyrrole ring, then $R_1$ must represent a substituent other than hydrogen or an unsubstituted alkyl group and when $R_1$ is hydrogen or alkyl and either X or Y is attached to a carbon in the 2-position of the pyrrole ring, then the phenyl substituent represented by either X or Y in the 2-position on the pyrrole ring must be substituted with at least one atom or group other than hydrogen.

DETAILED DESCRIPTION OF THE PREFERRED EMBODIMENTS

A preferred group of compounds of this invention are those wherein $R_3$ is $CF_3$; X and Y each represent a substituted phenyl group and $R_1$ and $R_2$ are described above.

Preparation of the formula I and II compounds of this invention can be achieved by a variety of synthesis routes utilizing various known starting materials. For example, a 2,4-bisaryl-5-(trifluoromethyl)-3-nitropyrrole can be prepared commencing with the bromination of a substituted or unsubstituted beta-nitrostyrene, such as p-chloro-beta-nitrostyrene. This reaction is conducted in the presence of a chlorinated hydrocarbon solvent at an elevated temperature to yield the formula III (substituted or unsubstituted-phenyl)-1,2-dibromo-2-nitroethane. The thus-prepared nitroethane derivative is then subjected to a dehalogenation treatment using a base such as pyridine, in the presence of a hydrocarbon solvent. This reaction is preferably conducted at an elevated temperature and yields the appropriately substituted or unsubstituted nitrobromostyrene of formula IV. Reaction of the nitrobromostyrene with an appropriately substituted formula V oxazolinone in the presence of a tri($C_1-C_4$ alkyl)amine and an organic solvent at an elevated temperature yields the formula I 2,4-bisaryl-5-(substituted)-3-nitropyrrole. These reactions are illustrated in Flow Diagram I.

From Flow Diagram I, it can also be seen that the formula I 2,4-bisaryl-5-(substituted)-3-nitropyrroles can be prepared by reaction of a substituted or unsubstituted beta-nitrostyrene with a formula V oxazolinone in the presence of a tri($C_1-C_4$ alkyl)amine and a solvent such as acetonitrile at an elevated temperature. The reaction yields the formula VI 2,4,5-substituted pyrrole corresponding to the oxazolinone and the beta-nitrostyrene used in the reaction. This 2,4,5-substituted pyrrole is then nitrated in the 3 position of the pyrrole ring, by reaction thereof with an excess of nitric acid in the presence of acetic anhydride. The reaction is conducted at ambient temperature between 15° C. to 30° C.

Preparation of N-substituted formula I diarylpyrroles can be achieved by reaction of the appropriately substituted formula I diarylpyrrole, wherein $R_1$ is hydrogen and X, Y, $R_2$ and $R_3$ are as described above, with an appropriate alkylating or acylating agent and a suitable base. For example, methyl iodide, ethyl iodide, chloromethyl ($C_1$-$C_4$) alkyl ether, acetylchloride, benzoyl bromide or the like and potassium t-butoxide. This reaction provides an arylpyrrole having the same substituents as the starting material, but in addition is substituted on the nitrogen with a methyl, ethyl, ($C_1$-$C_4$) alkoxymethyl, acetyl, benzoyl or similar substituent.

The reactions are illustrated in Flow Diagram I below.

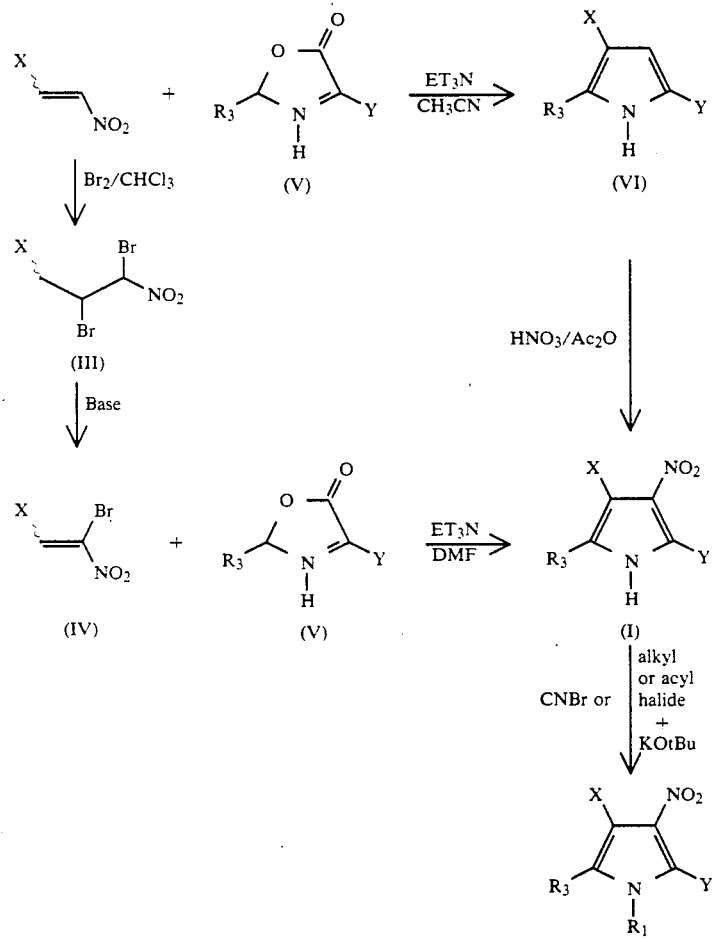

Flow Diagram 1

Synthesis of 2,4-Bis(aryl)-5-substituted-3-nitropyrroles

Preparation of 2,3-bis(aryl)-4-nitro-5-(substituted)-pyrroles can be achieved by reaction of an acetophenone, substituted or unsubstituted, with thionyl halide in the presence of an organic base such as pyridine. Thereafter, the reaction mixture is treated with aqueous sodium tetrafluoroborate to yield a formula VII N-α-(substituted or unsubstituted)-styrylpyridinium tetrafluoroborate. The formula VII styrylpyridinium tetrafluoroborate is then reacted with a formula V oxazolinone in the presence of a base, such as pyridine, at an elevated temperature to yield a formula VIII 2,3-bis(aryl)-5-substituted)pyrrole. The 2,3-bis(aryl)-5-(substituted)pyrrole is then reacted with nitric acid and acetic anhydride to obtain the 2,3-bis(aryl)-4-nitro-5-(substituted)-pyrrole of formula II. These reactions are illustrated in Flow Diagram II below.

Flow Diagram II
Synthesis of 2,3-Bis(aryl)-5-(substituted)-4-nitropyrroles

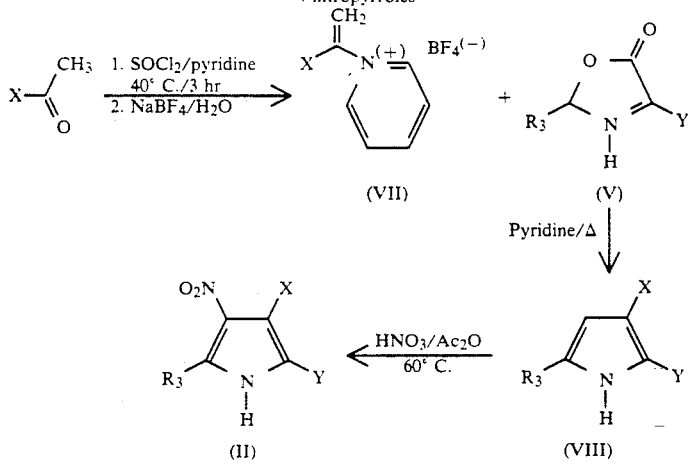

The 2,4-diaryl-5-(substituted)pyrrole-3-carbonitriles and 1-alkoxyalkyl derivatives thereof can be prepared by bromination of an appropriate cinnamonitrile in the presence of an inert chlorinated hydrocarbon solvent to obtain the corresponding formula IX dibromocinnamonitrile. This dibromocinnamonitrile is then converted to the corresponding α-bromo-cinnamonitrile of formula X by reaction with base, such as triethylamine, in the presence of anhydrous ether. Thereafter, the α-bromocinnamonitrile is reacted with a formula V oxazolinone in the presence of base, such as triethylamine and acetonitrile to obtain the formula I product. These reactions are illustrated in Flow Diagram III below.

To obtain the formula I or II diarylnitropyrrole or diarylpyrrolecarbonitrile wherein $R_1$ is alkoxyalkyl, the formula I or formula II diarylpyrrole in which $R_1$ is hydrogen and $R_2$, $R_3$, X and Y are as described above, is treated with an appropriate halodialkyl ether in the presence of a strong base, such as an alkali metal alkoxide and an inert organic solvent such as tetrahydrofuran. The reaction is illustrated in Flow Diagram III where Z is halogen. The reactions are illustrated in Flow Diagram III below.

Flow Diagram III
Synthesis of 2,4-Bis(aryl)-5-(substituted)-pyrrole-3-carbonitrile

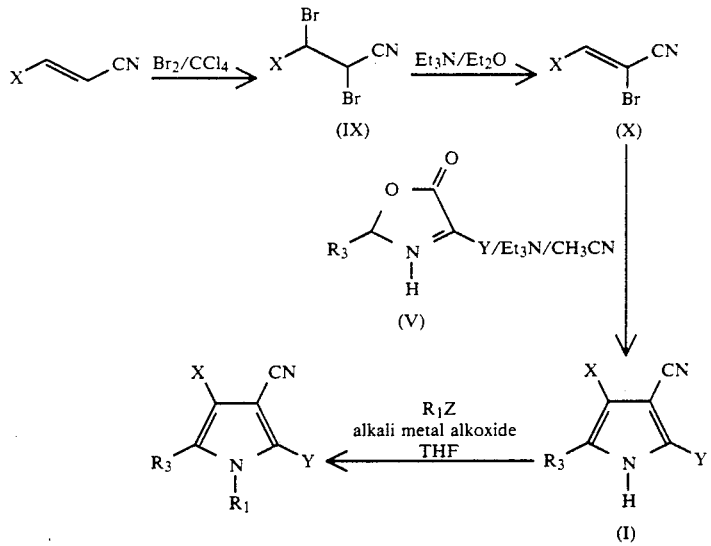

The compounds of this invention are useful as insecticidal and acaricidal agents. They are also effective for protecting crops, i.e. growing plants, trees, shrubs and the like, from the ravages of feeding insects and acarina.

In practice, the formula I and formula II compounds of the invention are generally found to be effective for controlling the above-said agricultural pests and for protecting crops from attack thereby, when applied at the rate of about 0.16 kg/ha to about 4.0 kg/ha to the foliage and stems of said plants sought to be protected, to the feeding ground of said pests, their habit or their breeding grounds.

The formula I and II diaryl nitropyrroles and pyrrolecarbonitriles of the invention can be formulated as suspension concentrates, compacted granules, dust concentrates, wettable powders, aqueous flowables, emulsifiable concentrates or the like and applied to a locus of treatment dispersed in a solid or liquid diluent.

The formula I and II diarylpyrroles and diarylpyrrolecarbonitriles of the invention can be formulated as wettable powders by grinding together about 5% to 25% by weight of the diarylpyrrole or diarylpyrrolecarbonitrile, 5% to 25% by weight of an anionic surfactant such as a dioctyl ester of sodium sulfosuccinic acid and about 10% to 50% by weight of an inert solid diluent such as montmorillonite, attapulgite, diatomaceous earth or the like. For application, the wettable powder is generally dispersed in water and applied to the plants or locus of treatment in the form of an aqueous spray containing from about 10 ppm to 10,000 ppm of the formula I or II pyrrole and preferably about 100 to 2000 ppm of said formula I or II diarylpyrrole.

A typical suspension concentrate formulation may be prepared by grinding together about 5% to 25% by weight of a formula I or II diarylpyrrole, about 5% to 20% by weight of an anionic surfactant such as dodecyl benzene sulfonic acid, about 1% to 5% by weight of a nonionic surfactant such as an ethylene oxide block copolymer having about 8 to 11 mols of ethoxylation, about 1% to 5% by weight of alkylphenol polyethylene oxide condensate with 9 to 10 mols of ethoxylation and q.s. to 100% with a petroleum aromatic solvent.

A preferred group of ethylene oxide/propylene oxide block copolymers for use in the compositions of this invention are butyl-ω-hydroxypoly(oxypropylene)-block polymer with poly(oxyethylene) having an average molecular weight in a range of 2,400 to 3,500, with α-butyl-γ-hydroxy-ethylene oxide-propylene oxide block copolymers having an HLB of 12 and a viscosity at 25° C. of 2000 CPS, (TOXIMUL® 8320, Stepan Chemical Co.) being a most preferred member of this class of emulsifiers.

Preferred alkylphenol polyethylene oxide condensates for use in the compositions of the invention include the nonylphenol ethoxylates, with nonylphenol ethoxylate (9 to 10 mols of ethylene oxide) (FLO MO® 9N, DeSoto, Inc. Sellers Chemical Div) being a most preferred member of this class of emulsifiers.

Among the preferred petroleum aromatic solvents useful in the preparation of suspension concentrates containing the formula I N-acylated arylpyrroles of the present invention are: aromatic hydrocarbon mixture ($C_8$ to $C_9$ aromatics, bp 148.9° C.) (TENNECO® T500/100); aromatic hydrocarbon mixture (distillation range 210°–288° C.) (PANASOL® AN-3N, Amoco); aromatic hydrocarbon mixture ($C_8$ to $C_9$ aromatics, distillation range 155°–173° C.) (AROMATIC® 100, Exxon); aromatic hydrocarbon mixture ($C_{10}$ to $C_{13}$ aromatics, distillation range 226°–279° C.) (AROMATIC® 200).

Flowable formulations can be prepared by admixing about 5% to 50% and preferably about 10% to 25% by weight of the formula I or II diarylpyrrole with about 2% to 3% by weight of a naphthalene sulfonic condensate, about 0.1% to 0.5% by weight of a nonionic nonylphenoxy polyethoxy ethanol, about 0.1% to 0.5% of xanthum gum, about 0.1% to 0.5% of a swelling clay such as bentonite, about 5% to 10% by weight of propylene glycol, about 0.1% to 0.5% by weight of a silicone antifoam agent, about 0.1% to 0.3% by weight of an aqeuous dipropylene glycol solution of 1,2-benzisothiazolin-3-one (preservative) and q.s. to 100% with water.

These and other advantages of the invention may become more apparent from the examples set forth below.

EXAMPLE 1

Preparation of 1-(4-Chlorophenyl)-1,2-dibromo-2-nitroethane

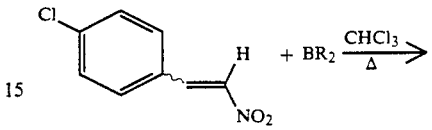

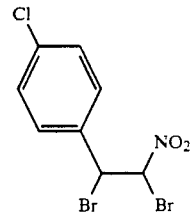

To a refluxing solution of p-chloro-beta-nitro styrene (12.0 g, 66 mmoles) and chloroform (200 mL) is slowly added bromine (3.4 mL, 66 mmoles) in chloroform (25 mL) over a 3 hour period. After addition is complete, the mixture is refluxed for an additional hour. The chloroform is removed by evaporation and the resulting oil crystallizes upon standing. This product is used in the next step without purification.

EXAMPLE 2

Preparation of beta-nitro-beta-bromostyrene

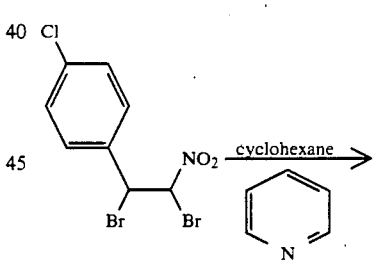

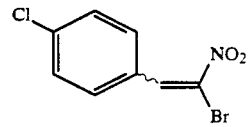

To a refluxing solution of 1-(4-chlorophenyl)-1,2-dibromo-2-nitroethane (from example 1) in cyclohexane (200 mL) is added a solution of pyridine (6 mL, 74 mmoles) in cyclohexane (200 mL) over a 1 hour period. The mixture is refluxed for an additional hour. The refluxing mixture is then extracted with approximately 200 mL of dilute HCl and 2×200 mL $H_2O$. The organic layer is dried over magnesium sulfate (anhydrous) filtered, and the solvent removed from the filtrate by evaporation to yield a yellow solid. The solid is recrystallized from cyclohexane to give beta-nitrobromostyrene.

EXAMPLE 3

Preparation of 2-p-Chlorophenyl-3-nitro 4-phenyl-5-(trifluoromethyl)pyrrole

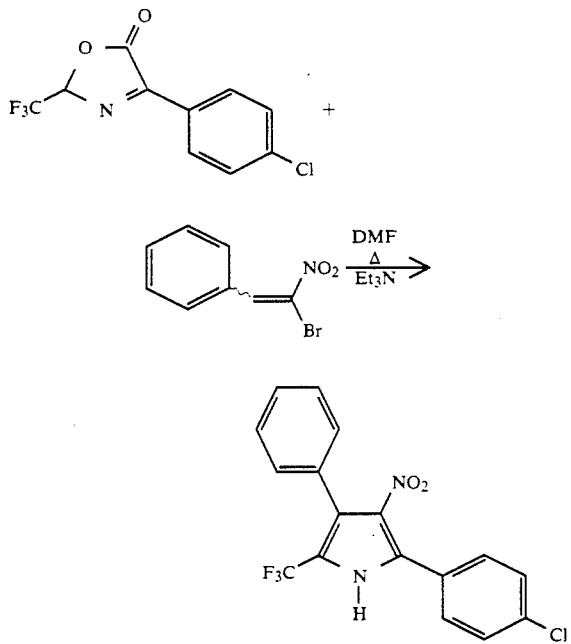

To a solution of 2-trifluoromethyl-4-(p-chlorophenyl)-3-oxazolin-5-one (7.36 g, 28 mmoles) and beta-nitro-beta-bromostyrene (6.27 g, 28 mmoles) in dimethylformamide (50 mL) is slowly added triethylamine (2.55 g, 25 mmoles). The solution exotherms to 56° C. and is then heated to reflux. Refluxing is continued until CO₂ evolution had ceased (approximately 1 hour).

The refluxing solution is cooled and extracted with 200 mL of diethyl ether/200 mL H₂O. The diethyl ether layer is dried over MgSO₄, filtered, and the filtrate is evaporated to yield an oil. Trituration with N-hexane yields the above said product as a pure solid (2.68 g, 27% yield), mp 158°–160° C.

EXAMPLE 4

Preparation of 2-(p-Trifluoromethylphenyl)-4-p-chloro-phenyl-5-trifluoromethylpyrrole

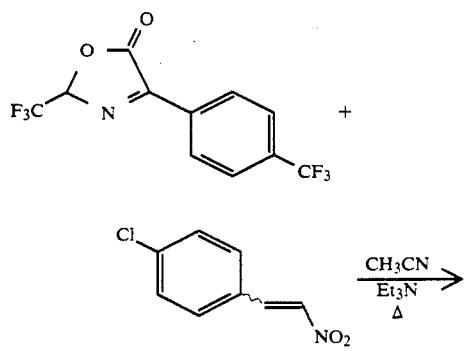

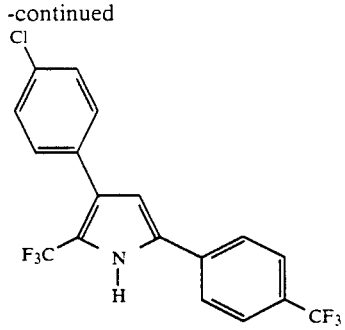

A solution containing 2-trifluoromethyl-4-trifluoromethylphenyl-3-oxazolin-5-one (1.86 g, 6.26 mmoles) and p-chloro-beta-nitrostyrene (1.38 g, 6.26 mmoles) in acetonitrile (25 mL) is warmed to 70° C. Triethylamine (0.65 g, 6.26 mmoles) is slowly added and the reaction solution is then refluxed until CO₂ evolution has ceased (approximately 1 hour).

The solvent is removed by evaporation. The reaction residue is chromatographed with 4:1 N-hexane:-ethyl acetate and the subject product is obtained as a brown solid (1.38 g, 55% yield).

EXAMPLE 5

Preparation of 3-(p-Chlorophenyl)-4-nitro-2-(trifluoromethyl-5-α,α,α-trifluoro-p-tolyl)pyrrole

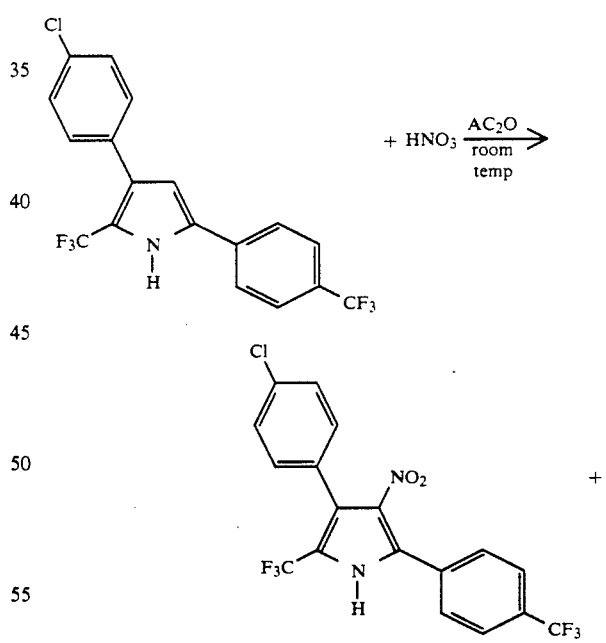

To a solution of 2-(p-trifluoromethylphenyl)-4-(p-chlorophenyl)-5-trifluoromethyl pyrrole (0.80 g, 2.05 mmoles) and acetic anhydride (20 mL) is slowly added 90% nitric acid (0.2 mL, 4.0 mmoles). The reaction solution is stirred one hour at room temperature and then extracted with 200 mL diethyl ether/100 mL H20. The diethyl ether layer is extracted with 100 mL dilute sodium bicarbonate, dried over magnesium sulfate (anhydrous), filtered, and filtrate evaporated. The residue is chromatographed with 4:1 n-hexane:-diethyl ether and the above-said product obtained as a yellow solid (0.60 g, 67% yield), mp 150°-155° C.

Following the procedures described in Flow Diagram I above and examples 1-3 or 4 and 5, but using the appropriately substituted beta-nitrostyrene and the appropriately substituted formula V oxazolinone, yields the following compounds:

2,4-bis(p-chlorophenyl)-3-nitro-5-(trifluoromethyl)pyrrole, mp 185°-190° C.;

2-(p-chlorophenyl)-4-(3,4-dichlorophenyl)-3-nitro-5-(trifluoromethyl)pyrrole, mp 205°-208° C.;

3-(p-chlorophenyl)-5-(3,4-dichlorophenyl)-4-nitro-2-(trifluoromethyl)pyrrole, mp 161°-163° C.;

2,4-bis(3,4-dichlorophenyl)-3-nitro-5-(trifluoromethyl)pyrrole, mp 72°-75° C.;

2-(p-chlorophenyl)-3-nitro-4-(m-nitrophenyl)-5-(trifluoromethyl)pyrrole, mp 205°-206° C.;

2-(p-chlorophenyl)-3-nitro-5-(trifluoromethyl)-4-(α,α,α-trifluoro-p-tolyl)-pyrrole, mp 174.5°-176° C.;

2-(p-chlorophenyl)-4-(3,4-dichlorophenyl)-3-nitro-5-(trifluoromethyl)pyrrole-1-carbonitrile, mp 98°-100° C.;

3-(2-bromo-4,5-dimethoxyphenyl)-5-(p-chlorophenyl)-4-nitro-2-(trifluoromethyl)pyrrole, mp 182°-185° C.;

p-[5-(p-chlorophenyl)=4-nitro-2-(trifluoromethyl)pyrrol-3-yl]benzonitrile, mp 245° (dec)C.;

2-(p-chlorophenyl)-3-nitro-4-p-tolyl-5-(trifluoromethyl)pyrrole, mp 197°-198° C.;

2-p-chlorophenyl-4-(o-chlorophenyl)-3-nitro-5-(trifluoromethyl)pyrrole, mp 200° C.;

2-(p-chlorophenyl)-4-(p-methoxyphenyl)-3-nitro-5-(trifluoromethyl)pyrrole, mp 172.5°-173° C.;

2-bromo-3,5-bis(p-chlorophenyl)-4-nitropyrrole, mp 175°-178° C.;

2-(p-chlorophenyl)-4-(4-methoxy-3-nitrophenyl)-3-nitro-5-(trifluoromethyl)pyrrole, mp 195°-198° C.;

2-(p-chlorophenyl)-4-(2,4-dichlorophenyl)-3-nitro-5-(trifluoromethyl)pyrrole, mp 195° C.

m-[5-(p-chlorophenyl)-4-nitro-2-(trifluoromethyl)pyrrol-3-yl]benzonitrile, mp 175°-178° C.;

2-(p-chlorophenyl)-4-(2,6-dichlorophenyl)-3-nitro-5-(trifluoromethylpyrrole, mp 237°-238.5° C.;

2-(p-chlorophenyl)-4-(3,4-difluorophenyl)-3-nitro-5-(trifluoromethyl)pyrrole, mp 145°-148° C.;

2-(p-chlorophenyl)-3-nitro-4-(p-nitrophenyl)-5-(trifluoromethyl)pyrrole, mp 224° C.;

2-(p-chlorophenyl)-4-(3,4-dichlorophenyl)-1-methyl-3-nitro-5-(trifluoromethyl)pyrrole, mp 134°-135° C.

EXAMPLE 6

Preparation of N-α-(4-chloro)styrylpyridinium tetrafluoroborate

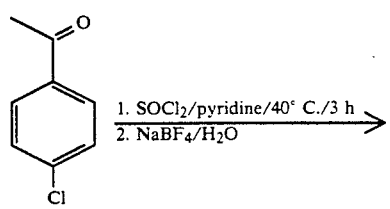

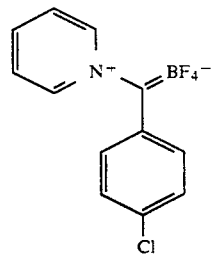

Thionyl chloride (36.5 mL, 0.5 mol) is added in a single portion, to a stirring solution of 4-chloroacetophenone (12.9 g, 0.1 mol) in pyridine (200 mL), causing an immediate exotherm to about 40° C. The dark solution is stirred at this temperature for an additional 3 hours, and then is cooled to ambient temperature. Most of the excess reagent is removed under reduced pressure to yield a thick, brown oil. Hexane is added to the residue and then decanted off. This procedure is repeated 3 times. The resulting dark residue is dissolved in a minimum amount of water. A small amount of dark, insoluble material is removed by filtration. A solution of sodium tetrafluoroborate (25 g, 0.23 mol) in water (75 mL) is added in a single portion, causing an immediate formation of a gummy precipitate which quickly becomes a discreet solid upon continued swirling and addition of ice. The solid is collected by filtration and washed with cold water and air-dried overnight. The resulting solid (27.2 g, 90%) is recrystallized from 2-propanol (300 mL; treated with activated charcoal) to yield the product as a shiny beige crystals.

EXAMPLE 7

Preparation of 2,3-bis(aryl)-5-(trifluoromethyl)pyrroles

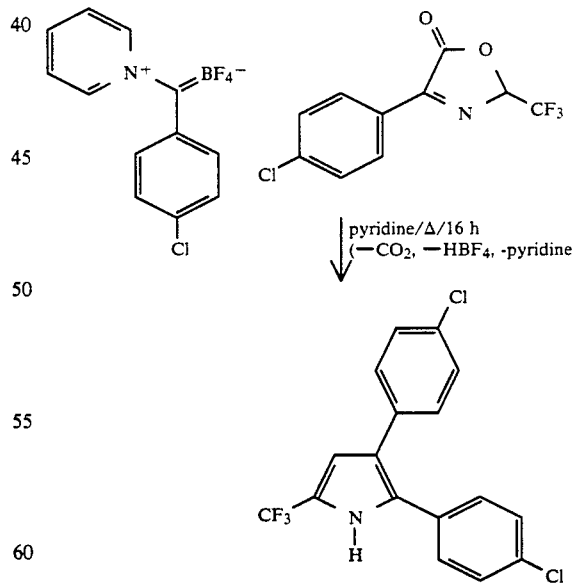

N-α-(4-chloro)styrylpyridinium tetrafluoroborate (5.2 g, 0.02 mol) is dissolved in pyridine (100 mL). In a single portion, the oxazolinone (4.4 g, 0.02 mol) is added, washed with a small portion of pyridine, causing an immediate ruby-red color and an exotherm. After allowing the temperature to drop to ambient, the solution is slowly brought to reflux (outgassing noted) and maintained for 16 hours. The dark, red-brown solution is cooled to room temperature, and solvent is removed under reduced pressure to yield a thick, brown semisolid which is partitioned between water (acidified with a small amount of HCl) and ether. The aqueous layer is extracted 4 times with ether and the combined ether extracts are washed twice with water and once with saturated sodium chloride. The solution is dried over $MgSO_4$ and ether is removed under reduced pressure to yield the product as a thick, dark oil. The product is purified via bulb-to-bulb distillation (130°–150° C., 0.2 mm Hg) to yield a thick, yellow oil (3.4 g, 48% theory) which solidifies upon prolonged storage.

EXAMPLE 8

Preparation of
2,3-bis(aryl)-4-nitro-5-(trifluoromethyl)pyrroles

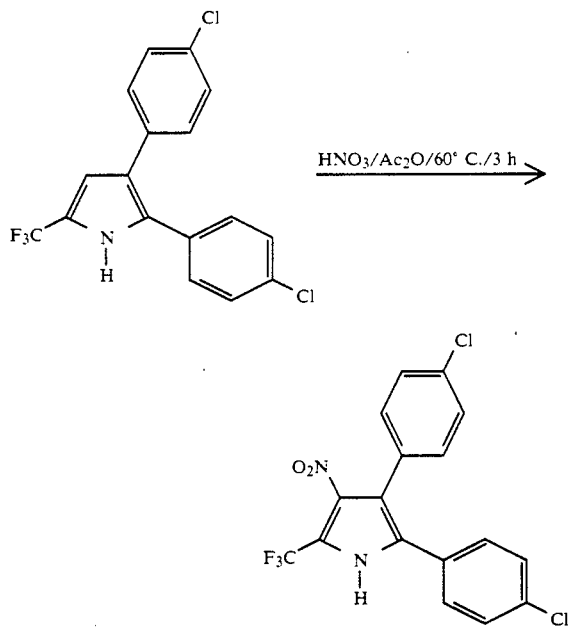

Nitric acid (0.25 mL of 90%; 0.005 mol) in acetic anhydride (5 mL) is added dropwise to a solution of 2,3-bis-(4-chlorophenyl)-5-(trifluoromethyl)pyrrole (1.8 g; 0.005 mol) in the same solvent (20 mL). After stirring 45 minutes at ambient temperature, an aliquot is removed and examined by HPLC which indicates only slight conversion to another more polar material. Another equivalent of nitric acid is added and the solution stirred 45 minutes more at ambient temperature prior to being heated briefly to 50° C., after which HPLC analysis indicates some starting material still remains. Another equivalent of nitric acid is added and the solution is heated for a short while at 60° C. Stirring is continued 16 hours at ambient temperature and solvent is removed under reduced pressure. Toluene is added to chase the remaining acetic anhydride. Trituration of the very thick, yellow oil with methyl cyclohexane causes formation of a solid. Heating causes all the solid to dissolve to a clear yellow solution which is treated with activated charcoal Upon cooling, a yellow precipitate forms. After storage in the freezer, the above-named solid product is collected by filtration, washed with cold hexanes, and dried on the filter (0.4 g; 20% theory) mp 193°–196° C.

Following the procedures of Flow Diagram III above and examples 6–8 and utilizing the appropriately substituted acetophenone to form the N-a-(4-substituted)styrylpyridinium tetrafluoroborate and thereafter reacting said tetrafluoroborate compound with an appropriately substituted oxazolinone yields the following compounds:

2-(p-chlorophenyl)-3-(3,4-dichlorophenyl)-4-nitro-5-(trifluoromethyl)pyrrole, mp 182°–185° C.;

2,3-bis(3,4-dichlorophenyl)-4-nitro-5-(trifluoromethyl)pyrrole, mp 168°–171° C.; and 2,3-bis(3,4-dichlorophenyl)-5-(trifluoromethyl)pyrrole, mp 90°–95° C.

EXAMPLE 9

Preparation of N-a-Bromo-p-chlorocinnamonitrile

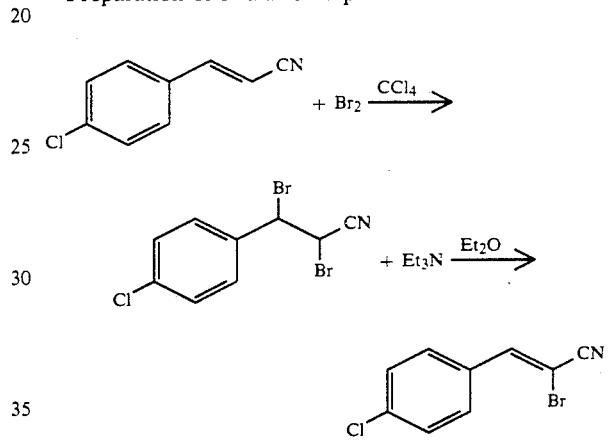

Bromine (16 g, 0.1 mol) is added dropwise to a solution of p-chlorocinnamonitrile in 100 mL of carbon tetrachloride over a 20 minute period. The reaction mixture is heated to refluxing temperature for 6 hours, cooled to room temperature and filtered to remove a small amount of insoluble solid. The filtrate is washed with 100 mL of 10% (w/v) aqueous sodium thiosulfate, 100 mL of water and 100 mL of saturated brine, then dried over magnesium sulfate, filtered and evaporated to give the dibromide as a yellow oil (30 g, 93%).

The oil is dissolved in 300 mL of anhydrous ether and triethylamine (10.1 g, 0.1 mol) is added to the solution at 0°–5° C. over a 20 minute period. After stirring for 2 hours at room temperature, the reaction mixture is filtered and the filtrate is evaporated to give α-bromo-p-chlorocinnamonitrile as a tan solid (13.9 g, 57.4% yield).

EXAMPLE 10

Preparation of
2,4-Bis(p-chlorophenyl)-5-(trifluoromethyl)pyrrole-3-carbonitrile

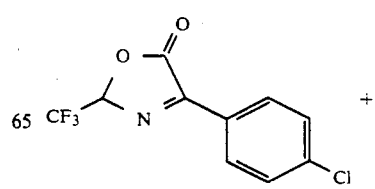

-continued

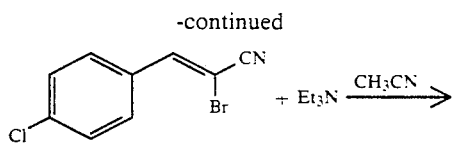

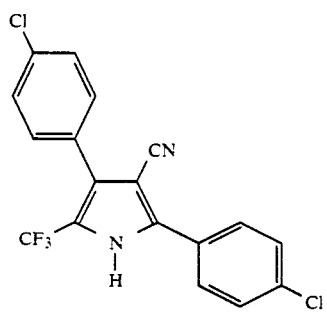

Triethylamine (1.1 g, 0.011 mol) is added dropwise to a mixture of 2-(trifluoromethyl)-4-(4-chlorophenyl)-3-oxazolin-5-one and α-bromo-p-chlorocinnamonitrile in 25 mL of acetonitrile and the mixture is stirred at room temperature for 18 hours. The reaction mixture is poured into 100 mL of water and extracted with two 30 mL portions of ethyl acetate. The combined extracts are washed with 30 mL of water, 30 mL of saturated brine, dried over magnesium sulfate, filtered and the solvent evaporated to leave a brown solid.

Trituration of the solid with hexanes and filtration gives the product as an off-white solid in 41% yield (1.55 g) mp >250° C.

Other 2,4-bis(aryl)-5-(substituted)pyrrole-3-carbonitriles that can be prepared by this procedure utilizing the appropriately substituted cinnamonitrile to obtain the desired α-bromo-(substituted)cinnamonitrile and reacting said α-bromo compound with the appropriate oxazolinone yields the following compounds:

4-(p-chlorophenyl)-2-[p-(1,1,2,2-tetrafluoroethoxy)-phenyl]-5-(trifluoromethyl)pyrrole-3-carbonitrile, mp 203°–204° C.;

4-(p-chlorophenyl)-2-(3,4-dichlorophenyl)-5-(trifluoromethyl)pyrrole-3-carbonitrile, mp 223°–224° C.;

5-bromo-2,4-bis(p-chlorophenyl)pyrrole-3-carbonitrile, mp >250° C.;

2-(p-chlorophenyl)-4-phenyl-5-(trifluoromethyl)pyrrole-3-carbonitrile, mp 249°–250° C. (dec);

2-(p-chlorophenyl)-4-(3,4-dichlorophenyl)-5-(trifluoromethyl)pyrrole-3-carbonitrile, mp 249°–250° C.;

4-(3,4-dichlorophenyl)-2-[p-(1,1,2,2-tetrafluoroethoxy)-phenyl]-5-(trifluoromethyl)pyrrole-3-carbonitrile, mp 218°–220° C.;

5-bromo-2,4-bis(p-chlorophenyl)pyrrole-3-carbonitrile, mp >250° C.;

2-(p-chlorophenyl)-4-(3,4-dichlorophenyl)-1-ethoxymethyl)-5-(trifluoromethyl)pyrrole-3-carbonitrile, yellow oil; and 2-(p-bromophenyl)-4-(3,4-dichlorophenyl)-5-(trifluoromethyl)pyrrole-3-carbonitrile, mp >225° C.

EXAMPLE 11

Preparation of 2,4-Bis(p-chlorophenyl)-1-(ethoxymethyl)-5-(trifluoromethyl)pyrrole-3-carbonitrile

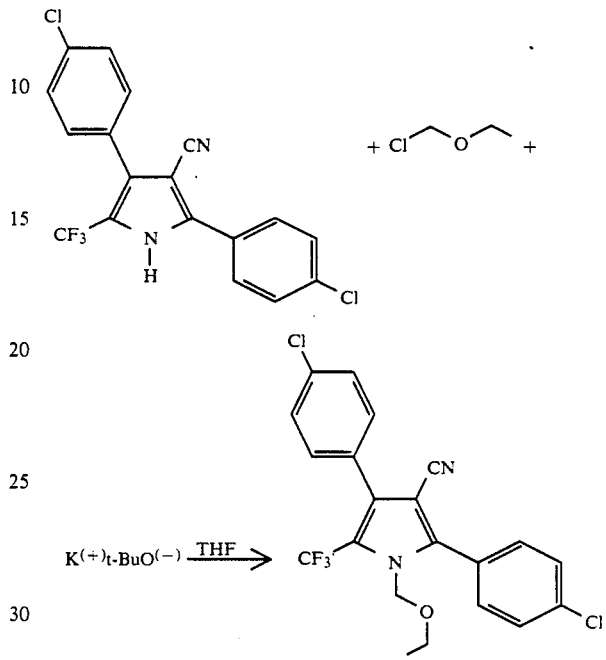

A partial solution of 2,4-bis(p-chlorophenyl)-5-(trifluoromethyl)pyrrole-3-carbonitrile (1.9 g, 0.005 mol) in 15 mL of tetrahydrofuran is added dropwise to a solution of potassium tert-butoxide (0.67 g, 0.006 mol) in 5 mL of tetrahydrofuran and the reaction mixture is stirred at room temperature for 30 minutes. Chloromethyl ethyl ether (0.47 g, 0.0055 mol) is added and the reaction mixture is stirred at room temperature for 3 hours.

The mixture is poured into 50 mL of water and extracted with two 30 mL portions of ethyl ether. The combined extracts are washed with 30 mL of water and 30 mL of saturated brine, dried over magnesium sulfate, filtered and the solvent removed under vacuum. The residue is recrystallized from 2-propanol to give the product as white crystals (1.42 g, 65%), mp 100°–101° C.

The following compounds can be prepared by this procedure using the appropriately substituted pyrrole-3-carbonitrile and the appropriate alkylating or acylating agent.

4-(p-chlorophenyl)-1-(ethoxymethyl)-2-[p-(1,2,2-tetrafluoroethoxy)phenyl]-5-(trifluoromethyl)pyrrole-3-carbonitrile, mp 108°–109° C.;

and tert-butyl-2,4-bis(p-chlorophenyl)-3-cyano-5-(trifluoromethyl)pyrrole-1-acetate, mp 175°–177° C.

Also, substituting the appropriate 2,4-bis(aryl)nitropyrrole for the 2,4-bis (p-chlorophenyl)-5-(trifluoromethyl)pyrrole-3-carbonitrile in the above example and using the appropriate halo ether yields the following 2,4-bis(aryl)nitropyrrole compounds:

3-(p-chlorophenyl)-5-(3,4-dichlorophenyl)-1-(ethoxymethyl)-4-nitro-2-pyrrole, amber resin;

2-(p-chlorophenyl)-4-(3,4-dichlorophenyl)-1-ethoxymethyl)-3-nitro-5-pyrrole, mp 121°–122.5° C.;

2-(p-chlorophenyl)-4-(3,4-dichlorophenyl)-1-(1-ethoxyethyl)-3-nitro-5-(trifluoromethyl)pyrrole, mp 115°-122° C.;

2-(p-chlorophenyl)-1-(ethoxymethyl-3-nitro-5-(trifluoromethyl)-4-(α,α,α-trifluoro-p-tolyl)pyrrole, mp 97.5°-100° C.

2,4-Bis-(p-chlorophenyl)-1-benzoyl-3-nitropyrrole;

2,4-Bis-(p-chlorophenyl)-1-(tert-butyloxycarbonylmethyl)-3-cyanopyrrole; and

2,-(p-chlorophenyl)-4-(3,4-dichlorophenyl)-1-(1-methoxyethyl)-3-nitropyrrole.

EXAMPLE 12

Preparation of 2,4-Bis(p-chlorophenyl)-3-cyano-5-(trifluoromethyl)-pyrrole-1-acetic acid, tert-butyl ester

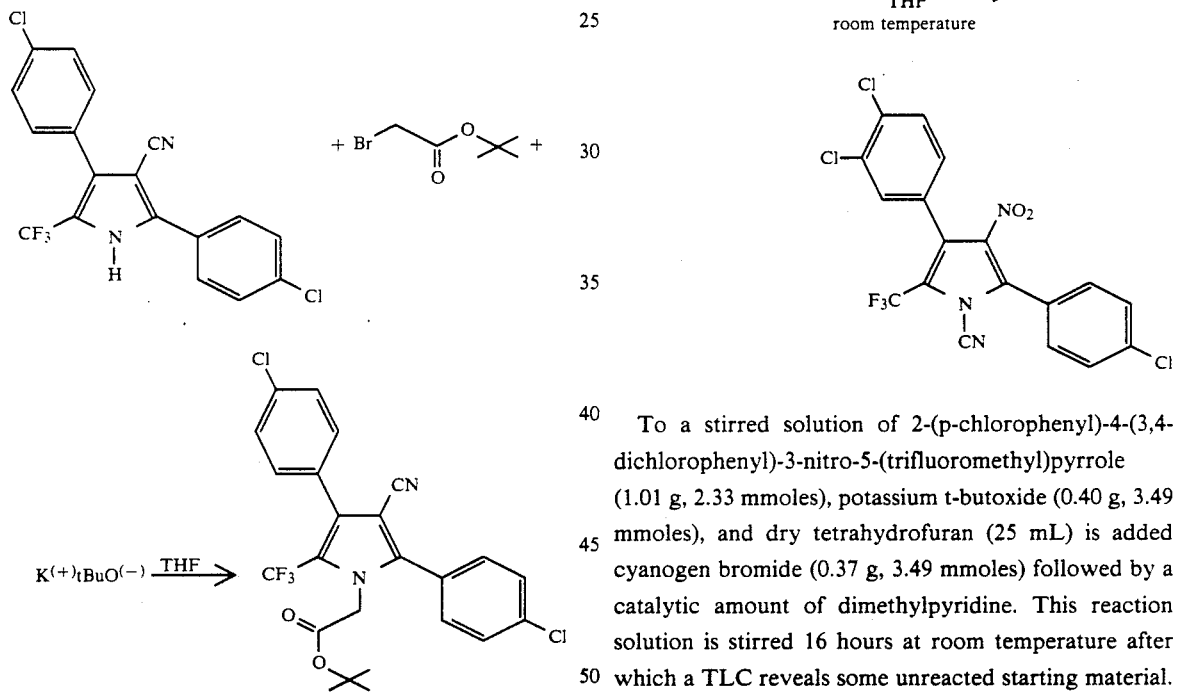

A solution of 2,4-bis(p-chlorophenyl)-3-cyano-5-(trifluoromethyl)pyrrole (1.9 g, 5 mmol) in 1 mL of tetrahydrofuran is added dropwise to a solution of potassium tert-butoxide (0.67 g, 6 mmol) in 10 mL of tetrahydrofuran and the mixture is stirred at room temperature for 15 minutes. tert-Butyl bromoacetate is added and the mixture is heated to refluxing temperature for 2 days.

The reaction mixture is poured into 40 mL of water and stirred for 30 minutes. The resulting solid is filtered off, washed with water and air dried. Recrystallization from 2-propanol gives a white solid in 30% yield; mp 175°-177° C.

EXAMPLE 13

Preparation of 2-(p-chlorophenyl)-4-(3,4-dichlorophenyl)-3-nitro-5-(trifluoromethyl)pyrrole-1-carbonitrile

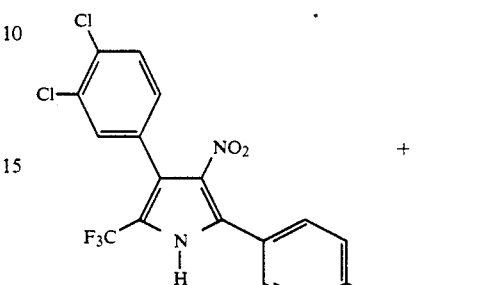

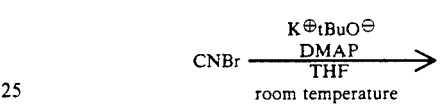

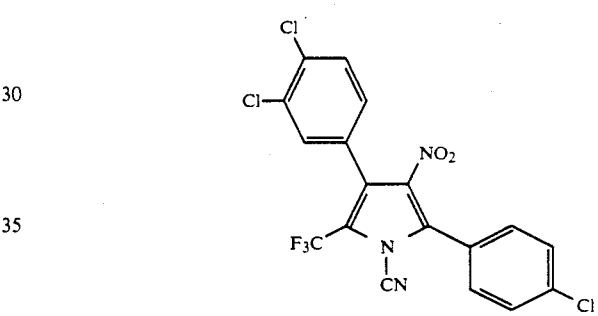

To a stirred solution of 2-(p-chlorophenyl)-4-(3,4-dichlorophenyl)-3-nitro-5-(trifluoromethyl)pyrrole (1.01 g, 2.33 mmoles), potassium t-butoxide (0.40 g, 3.49 mmoles), and dry tetrahydrofuran (25 mL) is added cyanogen bromide (0.37 g, 3.49 mmoles) followed by a catalytic amount of dimethylpyridine. This reaction solution is stirred 16 hours at room temperature after which a TLC reveals some unreacted starting material. An additional amount of potassium t-butoxide (0.4 g, 3.49 mmoles) and cyanogen bromide (3.70 g, 3.49 mmoles) are added and reaction is complete after 1 hour of room temperature stirring.

Diethyl ether (100 mL) is added to the reaction solution and the resulting solution is extracted with water (100 mL). The aqueous portion is discarded. The diethyl ether layer is dried over magnesium sulfate, filtered, and the ether removed by evaporation to yield a residue. Boiling of this reaction residue in n-hexane (200 mL) followed by filtration and evaporation of the hexane solution yields the desired product (0.47 g, yellow solid, 44% yield, mp 98°-100° C.

EXAMPLE 14

Preparation of
2,4-Bis(3,4-dichlorophenyl)-3-bromo-5-nitropyrrole

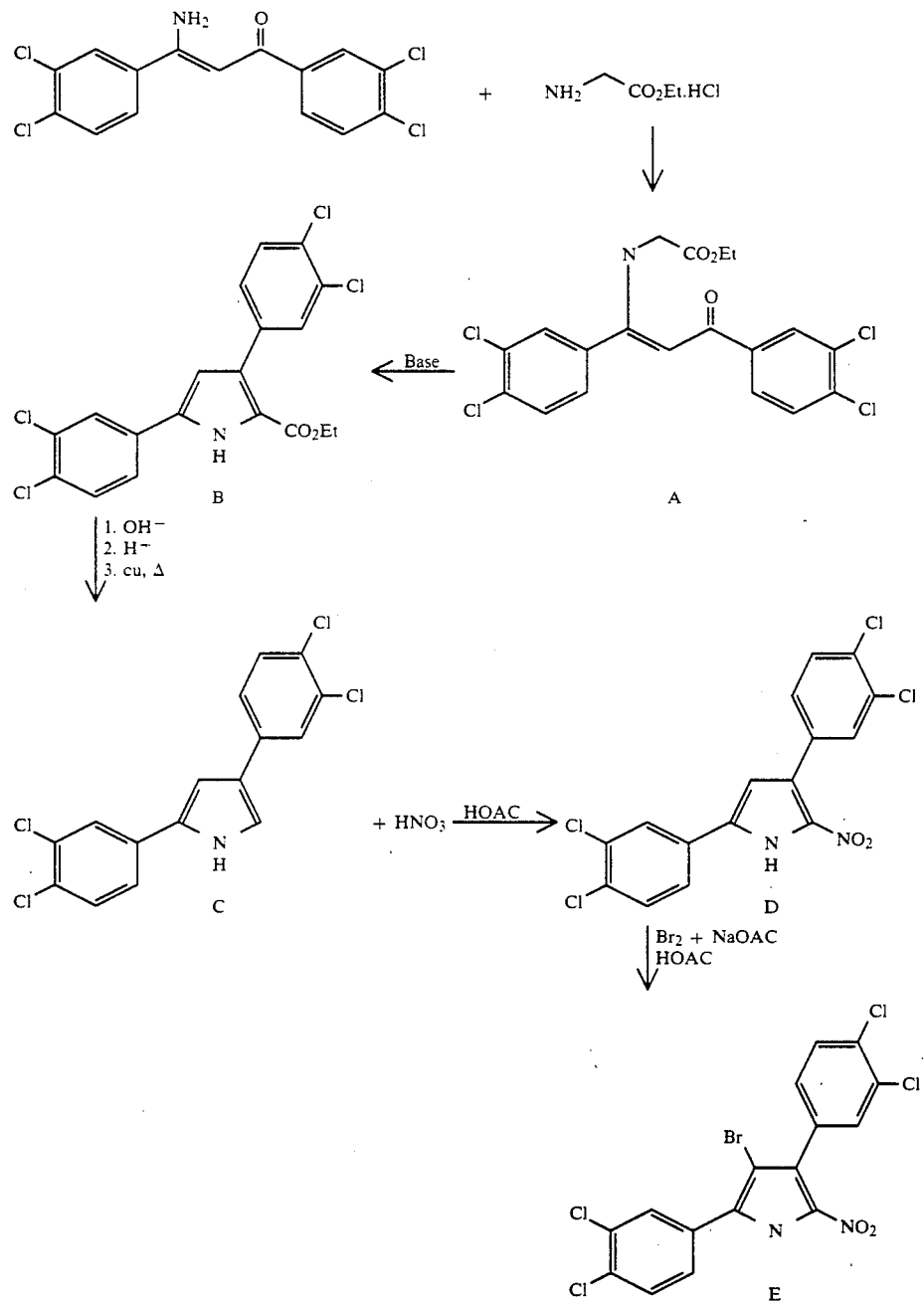

Condensation of ethylglycinate with the β-aminoenone of 1,3-di(3,4-dichlorophenyl)-1,3-propanedione followed by treatment of the resulting product A with sodium ethoxide according to the procedure of Alberola,[1] et al leads to 2,4-bis(3,4-dichlorophenyl)-5-carboethoxypyrrole B. Hydrolysis of the ester of B with base followed by acidification and copper/quinoline decarboxylation leads to 2,4-bis(3,4-dichlorophenyl)-pyrrole C. Nitration of C using nitric acid in acetic anhydride leads to 2,4-bis(3,4-dichlorophenyl)-5-nitropyrrole D.

[1] A. Alberola, J. Andres, A. Gonzales, R. Pedrosa, M. Vicente, Heterocycles, 31., 1049 (1990).

Bromination of D using bromine in acetic acid containing anhydrous sodium acetate leads to 2,4-bis-(3,4-dichlorophenyl)-3-bromo-5-nitropyrrole E.

EXAMPLE 15

Preparation of
2,4-Bis(p-chlorophenyl)-3-bromo-5-cyanopyrrole

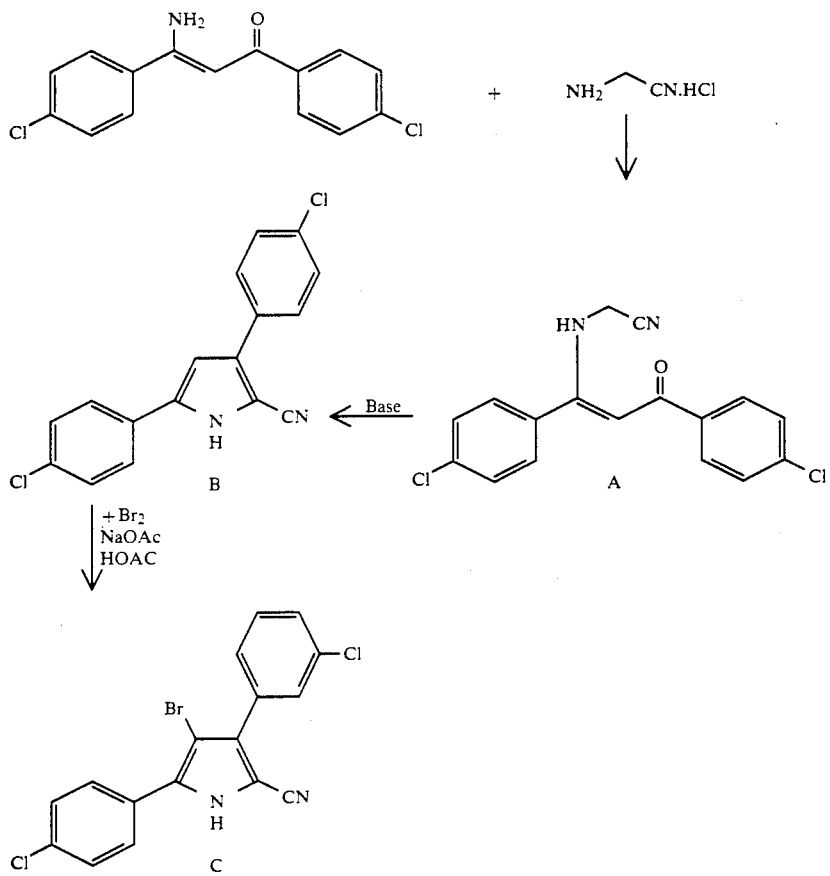

Condensation of the β-aminoenone of 1,3-di-(p-chlorophenyl)-1,3-propanedione with aminoacetonitrile in refluxing ethanol followed by evaporation of the solvent, slurrying of the residue in tetrahydrofuran and filtering to remove inorganic salts and evaporation gives the glycinonitrile derivative A.

Treatment of A with a base such as sodium ethoxide or pyridine or by refluxing in DMF induces cyclization to 2,4-bis(p-chlorophenyl)-5-cyanopyrrole.

Bromination of 2,4-bis(p-chlorophenyl)-5-cyanopyrrole is accomplished by treatment with 1 equivalent of bromine in acetic acid in the presence of anhydrous sodium acetate yields the desired product (0.47 g, yellow solid, 44% yield, mp 98°-100° C.

EXAMPLE 16

Preparation of Diarylpyrrolecarbonitriles and nitropyrroles as insecticidal agents Insecticidal evaluations are conducted with solutions of test compounds dissolved or dispersed in 50 acetone/water mixtures. The test compound is technical material dissolved or dispersed in said acetone/water mixtures in sufficient amount to provide the concentrations set forth in Table I below.

All concentrations reported herein are in terms of active ingredient. All tests are conducted in a laboratory maintained at about 27° C. The rating system employed is as follows:

| Rating System | |
|---|---|
| 0 = no effect | 5 = 56-65% kill |
| 1 = 10-25% kill | 6 = 66-75% kill |
| 2 = 26-35% kill | 7 = 76-85% kill |
| 3 = 36-45% kill | 8 = 86-99% kill |
| 4 = 46-55% kill | 9 = 100% kill |
| | R = reduced feeding |

The test species of insects used in the present evaluations along with specific test procedures are described below.

*Heliothis virescens,* 3rd instar tobacco budworm

Cotton cotyledons are dipped in the test solution and allowed to dry in a hood. When dry, each is cut into quarters and 10 sections placed individually in 30 mL plastic medicine cups containing a 5-7 mm long piece of damp dental wick. One 3rd-instar caterpillar is added to each cup and a cardboard lid placed on the cup. Treatments are maintained for 3 days before mortality counts and estimates of reduction in feeding damage are made.

*Spodoptera eridania,* 3rd instar larvae, southern armyworm

A sieva lima bean leaf expanded to 7-8 cm in length is dipped in the test suspension with agitation for 3 seconds and placed in a hood to dry. The leaf is then placed in a 100×10 mm petri dish containing a damp filter paper on the bottom and ten 3rd instar caterpillars. The dish is maintained for 3 days before observations are made of mortality, reduced feeding, or any interference with normal moulting and held for 2 additional days for a final 5 day reading.

*Spodoptera eridania*, 7-day residual

The plants treated in the above test are maintained under high intensity lamps in the greenhouse for 7 days. These lamps duplicate the effects of a bright sunny day in June in New Jersey and are kept on for a 14 hour day length. After 7 days, the foliage is sampled and assayed as in the above test for southern armyworms.

*Blattella germanica*, bait test, adult male German cockroach

A 0.1% bait is prepared by pipetting 1 mL of a 1,000 ppm solution of the test compound in acetone onto 1 g of cornmeal in a 30 mL wide-mouth bottle. The bait is dried by passing a gentle stream of air into the bottle. The bait is placed in a 1 pint wide-mouth Mason jar and ten adult male cockroaches are added. A screen lid is placed on the jar and a small piece of cotton soaked in 10% honey is put on the top of the screen lid. Mortality counts are made after 3 days.

*Blatella germanica*, residue test, adult male German cockroach

One mL of a 1,000 ppm acetone solution of the test material is pipetted slowly over the bottom of a 150×15 mm petri dish so as to give as uniform coverage as possible. After the deposit has dried, 10 adult male cockroaches are placed in each dish and the lid is added. Mortality counts are made after 3 days.

*Empoasca abrupta*, adults, western potato leafhopper

A Sieva lima bean leaf about 5 cm long is dipped in the test solution for 3 seconds with agitation and placed in a hood to dry. The leaf is placed in a 100×10 petri dish containing a moist filter paper on the bottom. About 10 adult leafhoppers are added to each dish and the treatments are kept for 3 days before mortality counts are made.

Data obtained are reported in Table I below.

TABLE I

Evaluation of diarylpyrrolecarbonitriles and diarylnitropyrroles as insecticidal agents

| Compound | Rate ppm | Budworm 3rd | Armyworm Day 3 | Armyworm Day 5 | Leafhopper contact | Cockroach Bait | Cockroach Residue |
|---|---|---|---|---|---|---|---|
| 2,3-Bis-(p-chlorophenyl)-4-nitro-5-(trifluoromethyl)-pyrrole | 1000 | — | 9 | 9 | 0 | 9 | 9 |
| | 100 | 9 | 9 | 9 | 9 | 9 | 4 |
| | Resi | — | 9 | 9 | — | — | — |
| 2-(p-Chlorophenyl)-3-(3,4-dichlorophenyl)-4-nitro-5-(trifluoromethyl)pyrrole | 1000 | 9 | 9 | 9 | — | 0 | 9 |
| | 100 | 9 | 9 | 9 | 9 | 0 | 0 |
| | Resi | — | 9 | 9 | — | — | — |
| 2-(p-Chlorophenyl)-3-nitro-4-(m-nitrophenyl)-5-(trifluoromethyl)pyrrole | 1000 | 9 | 9 | 9 | — | 4 | 9 |
| | 100 | 9 | 8 | 9 | 7 | — | 2 |
| | Resi | — | 9 | 9 | — | — | — |
| 2-(p-Chlorophenyl)-4-(3,4-dichlorophenyl)-1-(ethoxymethyl)-3-nitro-5-(trifluoromethyl)pyrrole | 1000 | 9 | 9 | 9 | — | 6 | 0 |
| | 100 | 9 | 9 | 9 | 0 | 0 | — |
| | Resi | — | 9 | 9 | — | — | — |
| 2-(p-Chlorophenyl)-3-nitro-5-(trifluoromethyl)-4-(alpha, alpha, alpha)trifluoro-p-tolyl)pyrrole | 1000 | 9 | 9 | 9 | — | 5 | 4 |
| | 100 | 9 | 9 | 9 | 9 | 0 | 0 |
| | Resi | — | 9 | 9 | — | — | — |
| 2-(p-Chlorophenyl)-4-(3,4-dichlorophenyl)-3-nitro-5-(trifluoromethyl)pyrrole-1-carbonitrile | 1000 | 9 | 9 | 9 | 0 | 4 | 9 |
| | 100 | 9 | 9 | 9 | 9 | 0 | 0 |
| | Resi | — | 9 | 9 | — | — | — |
| 3-(2-Bromo-4,5-(dimethoxyphenyl)-5-(p-chlorophenyl)-4-nitro-2-(trifluoromethyl)-pyrrole | 1000 | 0 | 9 | 9 | — | 4 | 0 |
| | 100 | 0 | 0 | 0 | 0 | 4 | 0 |
| | Resi | — | 9 | 9 | — | — | — |
| 2-(p-Chlorophenyl)-4-(3,4-dichlorophenyl)-1-(1-ethoxymethyl-3-nitro-5-(trifluoromethyl)pyrrole | 1000 | 9 | 9 | 9 | — | 0 | 0 |
| | 100 | 9 | 9 | 9 | 5 | 0 | 0 |
| | 10 | 0 | 9 | 9 | 0 | — | — |
| | 1 | — | — | — | — | — | — |
| | Resi | — | 9 | 9 | — | — | — |
| 2-(p-Chlorophenyl)-3-nitro-4-(p-nitrophenyl)-5-(trifluoromethyl)pyrrole | 1000 | 9 | 9 | 9 | — | 0 | 8 |
| | 100 | 9 | 9 | 9 | 8 | 0 | 0 |
| | Resi | — | 9 | 9 | — | — | — |
| 2-(p-Chlorophenyl)-4-(3,4-dichlorophenyl)-1-methyl)-3-nitro-5-(trifluoromethyl)-pyrrole | 1000 | 9 | 9 | 9 | — | 0 | 1 |
| | 100 | 9 | 9 | 9 | 5 | 0 | 0 |
| | Resi | — | 9 | 9 | — | — | — |
| 2,3-Bis-3,4-dichlorophenyl)-4-nitro-5-(trifluoromethyl)-pyrrole | 1000 | 9 | 9 | 9 | — | 6 | 5 |
| | 100 | 7 | 0 | 9 | 0 | — | 7 |
| | Resi | — | 4 | 4 | — | — | — |
| 2-(p-Chlorophenyl)-3-nitro-4-phenyl-5-(trifluoromethyl)pyrrole | 1000 | 9 | 9 | 9 | — | 0 | 0 |
| | 100 | 0 | 9 | 9 | 0 | — | — |
| | Resi | — | 9 | 9 | — | — | — |
| 2-4-Bis(p-chlorophenyl)-3-nitro-5-(trifluoromethyl)-pyrrole | 1000 | 9 | 9 | 9 | — | 9 | 9 |
| | 100 | 9 | 9 | 9 | 8 | 9 | 0 |
| | Resi | — | 9 | 9 | — | — | — |
| 2-(p-Chlorophenyl)-4-(3,4-dichlorophenyl)-3-nitro-5-(trifluoromethyl)pyrrole | 1000 | 9 | 9 | 9 | — | 9 | 9 |
| | 100 | 9 | 9 | 9 | 9 | 9 | 0 |
| | Resi | — | 9 | 9 | — | — | — |
| 3-(p-Chlorophenyl)-5-(3,4-dichlorophenyl)-4-nitro-2-(trifluoromethyl)pyrrole | 1000 | 9 | 9 | 9 | — | 9 | 7 |
| | 100 | 9 | 9 | 9 | 7 | 7 | 0 |
| | Resi | — | 9 | 9 | — | — | — |

TABLE I-continued

Evaluation of diarylpyrrolecarbonitriles and diarylnitropyrroles as insecticidal agents

| Compound | Rate ppm | Budworm 3rd | Armyworm Day 3 | Armyworm Day 5 | Leafhopper contact | Cockroach Bait | Cockroach Residue |
|---|---|---|---|---|---|---|---|
| 3-(p-Chlorophenyl)-5-(3,4-dichlorophenyl-1-(ethoxy-methyl)-4-nitro-2-(tri-fluoromethyl)pyrrole | 1000<br>100<br>Resi | 9<br>9<br>— | 9<br>9<br>9 | 9<br>9<br>9 | —<br>6<br>— | —<br>0<br>— | —<br>0<br>— |
| 2,4-Bis-(3,4-dichlorophenyl)-3-nitro-5-(trifluoromethyl)-pyrrole | 1000<br>100<br>Resi | 9<br>9<br>— | 9<br>9<br>9 | 9<br>9<br>9 | —<br>9<br>— | 0<br>0<br>— | 3<br>0<br>— |
| 3-(p-Chlorophenyl)-4-nitro-2-(trifluoromethyl)-5-(alpha, alpha, alpha-tri-fluoro-p-tolyl)pyrrole | 1000<br>100<br>Resi | 9<br>9<br>— | 9<br>9<br>9 | 9<br>9<br>9 | —<br>9<br>— | 9<br>0<br>— | 2<br>—<br>— |
| 2-(p-Chlorophenyl)-1-(ethoxymethyl)-3-nitro-5-(trifluoromethyl)-4-(alpha, alpha, alpha-tri-fluoro-p-tolyl)pyrrole | 1000<br>100<br>Resi | 9<br>9<br>— | 9<br>9<br>9 | 9<br>9<br>9 | —<br>9<br>— | 0<br>—<br>— | 0<br>—<br>— |
| p-[-5-(p-Chlorophenyl)-4-nitro-2-(trifluoro-methyl)pyrrol-3-yl]-benzonitrile | 1000<br>100<br>Resi | 9<br>9<br>— | 9<br>9<br>0 | 9<br>9<br>0 | —<br>0<br>— | 0<br>—<br>— | 0<br>—<br>— |
| 2-(p-Chlorophenyl)-3-nitro-4-p-tolyl-5-(trifluoro-methyl)pyrrole | 1000<br>100<br>Resi | 0<br>0<br>— | 9<br>0<br>— | 0<br>0<br>— | —<br>0<br>— | 0<br>—<br>— | 0<br>—<br>— |
| 2-(p-Chlorophenyl)-4-(o-chlorophenyl)-3-nitro-5-(trifluoromethyl)pyrrole | 1000<br>100<br>Resi | 9<br>0<br>— | 9<br>9<br>9 | 9<br>9<br>9 | —<br>8<br>— | 0<br>—<br>— | 2<br>—<br>— |
| 2-(p-Chlorophenyl)-4-(p-methoxyphenyl)-3-nitro-5-(trifluoro-methyl)pyrrole | 1000<br>100<br>Resi | 0<br>0<br>— | 9<br>0<br>— | 9<br>0<br>— | —<br>0<br>— | 0<br>—<br>— | 0<br>—<br>— |
| 2-Bromo-3,5-bis(p-chlorophenyl-4-nitro-pyrrole | 1000<br>100<br>Resi | 9<br>9<br>— | 9<br>9<br>— | 9<br>9<br>— | —<br>5<br>— | 0<br>—<br>— | 5<br>0<br>— |
| 2-(p-Chlorophenyl)-4-(4-methoxy-3-nitro-phenyl-3-nitro-5-(tri-fluoromethyl)pyrrole | 1000<br>100<br>Resi | 9<br>9<br>— | 9<br>—<br>9 | 9<br>0<br>9 | —<br>0<br>— | 4<br>—<br>— | 0<br>0<br>— |
| 2-(p-Chlorophenyl)-4-(2,4-dichlorophenyl)-3-nitro-5-(trifluoro-methyl)pyrrole | 1000<br>100<br>Resi | 0<br>0<br>— | 9<br>9<br>9 | 9<br>9<br>9 | —<br>6<br>— | 0<br>—<br>— | 0<br>—<br>— |
| m-[5-(p-Chlorophenyl)-4-nitro-2-(trifluoro-methyl)pyrrol-3-yl]-benzonitrile | 1000<br>100<br>Resi | 9<br>9<br>— | 9<br>9<br>9 | 9<br>9<br>9 | —<br>9<br>— | 0<br>—<br>— | 9<br>0<br>— |
| 2-(p-Chlorophenyl)-4-(2,6-dichlorophenyl)-3-nitro-5-(trifluoro-methyl)pyrrole | 1000<br>100<br>Resi | 9<br>3<br>— | 9<br>9<br>9 | 9<br>9<br>9 | —<br>0<br>— | —<br>—<br>— | —<br>—<br>— |
| 2-(p-Chlorophenyl)-4-(3,4-difluorophenyl)-3-nitro-5-(trifluoromethyl)pyrrole | 1000<br>100<br>Resi | 9<br>9<br>— | 9<br>9<br>9 | 9<br>9<br>9 | 0<br>9<br>— | 9<br>0<br>— | 9<br>7<br>— |

Resi - residual

EXAMPLE 17

Evaluation of diarylpyrrolecarbonitriles and nitropyrroles as insecticidal and acaricidal agents In these tests evaluations are performed using technical material dissolved in 50/50 acetone water mixtures.

*Tetranychus urtica* (P-resistant strain), 2-spotted spider mite

Sieva lima bean plants with primary leaves expanded to 7-8 cm are selected and cut back to one plant per pot. A small piece is cut from a leaf taken from the main colony and placed on each leaf of the test plants. This is done about 2 hours before treatment to allow the mites to move over to the test plant and lay their eggs. The size of the cut piece is varied to obtain about 100 mites per leaf. At the time of the treatment, the piece of leaf used to transfer the mites is removed and discarded. The mite-infested plants are dipped in the test formulation for 3 seconds with agitation and set in the hood to dry. Plants are kept for 2 days before estimates of adult kill are made using the first leaf. The second leaf is kept on the plant for another 5 days before observations are made of the kill of eggs and/or newly emerged nymphs.

*Diabrotic undecimpunctata howardi*, 3rd instar southern corn rootworm

One cc of fine talc is placed in a 30 mL wide-mouth screw-top glass jar. One mL of the appropriate acetone solution is pipetted onto the talc so as to provide 1.25 and 0.25 mg of active ingredient per jar. The jars are set under a gentle air flow until the acetone is evaporated. The dried talc is loosened, 1 cc of millet seed is added to serve as food for the insects and 25 mL of moist soil is added to each jar. The jar is capped and the contents thoroughly mixed on a Vortex Mixer. Following this, 10 3rd instar rootworms are added to each jar and the jars are loosely capped to allow air exchange for the larvae. The treatments are held for 6 days before mortality counts are made. Missing larvae are presumed dead, since they decompose rapidly and can not be found. The concentrations used in this test correspond approximately to 50 and 10 kg/ha, respectively.

Data obtained are reported in Table II below.

TABLE II

Evaluation of diaryl pyrrole carbonitriles and nitropyrroles as insecticidal and acaricidal agents

| Compound | Rate ppm | p-Resistant mites | | | Rootworm |
|---|---|---|---|---|---|
| | | Adult | Egg | Nymph | |
| 2-3-Bis-(p-chlorophenyl)-4-nitro-5-(trifluoromethyl)-pyrrole | 300 | 0 | 0 | 0 | — |
| | 100 | — | — | — | — |
| | 50 | — | — | — | 9 |
| 2-(p-Chlorophenyl)-3-(3,4-dichlorophenyl)-4-nitro-5-(trifluoromethyl)pyrrole | 300 | 9 | 9 | — | — |
| | 100 | 9 | 8 | 8 | — |
| | 50 | — | — | — | 9 |
| 2-3-Bis(3,4-dichlorophenyl)-4-nitro-5-(trifluoromethyl)-pyrrole | 300 | 9 | 0 | 9 | — |
| | 100 | 7 | 0 | 0 | — |
| | 50 | — | — | — | 9 |
| 2-(p-Chlorophenyl)-3-nitro-4-(m-nitrophenyl)-5-(trifluoromethyl)pyrrole | 300 | 0 | 0 | 0 | — |
| | 100 | — | — | — | — |
| | 50 | — | — | — | 9 |
| 2-(p-Chlorophenyl)-4-(3,4-dichlorophenyl)-1-(ethoxymethyl)-3-nitro-5-(trifluoromethyl)pyrrole | 300 | 0 | 0 | 0 | — |
| | 100 | — | — | — | — |
| | 50 | — | — | — | 9 |
| 2-(p-Chlorophenyl)-3-nitro-5-(trifluoromethyl)-4-(alpha, alpha, alpha-trifluoro-p-tolyl)pyrrole | 300 | 9 | 0 | 9 | — |
| | 100 | 7 | 5 | 7 | — |
| | 50 | — | — | — | 5 |
| 2-(p-Chlorophenyl)-4-(3,4-dichlorophenyl)-3-nitro-5-(trifluoromethyl)pyrrole-1-carbonitrile | 300 | 9 | 0 | 8 | — |
| | 100 | 8 | 8 | 0 | — |
| | 50 | — | — | — | 5 |
| 2-(p-Chlorophenyl)-4-(3,4-dichlorophenyl)-1-ethoxymethyl)-3-nitro-5-(trifluoromethyl)pyrrole | 300 | 7 | 7 | 0 | — |
| | 100 | 0 | 6 | 0 | — |
| | 50 | — | — | — | 9 |
| 2-(p-Chlorophenyl)-3-nitro-4-(p-nitrophenyl)-5-(trifluoromethyl)pyrrole | 300 | 5 | 0 | 0 | — |
| | 100 | 5 | 0 | 0 | — |
| | 50 | — | — | — | 8 |
| 2-(p-Chlorophenyl)-4-(3,4-dichlorophenyl)-3-nitro-5-(trifluoromethyl)pyrrole | 300 | 9 | 8 | 9 | — |
| | 100 | 6 | 0 | 0 | — |
| | 50 | — | — | — | — |
| 3-(p-Chlorophenyl)-5-(3,4-dichlorophenyl)-4-nitro-2-(trifluoromethyl)pyrrole | 300 | 0 | 0 | 6 | — |
| | 100 | — | — | — | — |
| | 50 | — | — | — | — |
| 3-(p-Chlorophenyl)-5-(3,4-dichlorophenyl-1-(ethoxymethyl)-4-nitro-2-(trifluoromethyl)pyrrole | 300 | 0 | 0 | 0 | — |
| | 100 | — | — | — | — |
| | 50 | — | — | — | — |
| 2,4-Bis(3,4-dichlorophenyl)-3-nitro-5-(trifluoromethyl)-pyrrole | 300 | 0 | 0 | 0 | — |
| | 100 | 8 | 0 | 9 | — |
| | 50 | — | — | — | — |
| 3-(p-Chlorophenyl)-4-nitro-2-(trifluoromethyl)-5-(alpha, alpha, alpha-trifluoro-p-tolyl)pyrrole | 300 | 0 | 0 | 0 | — |
| | 100 | — | — | — | — |
| | 50 | — | — | — | 9 |
| 2-(p-Chlorophenyl)-1-ethoxymethyl)-3-nitro-5-(trifluoromethyl)-4-(alpha, alpha, alpha-trifluoro-p-tolyl)pyrrole | 300 | 0 | 0 | 0 | — |
| | 100 | — | — | — | — |
| | 50 | — | — | — | 8 |
| p-[-5-(p-Chlorophenyl)-4-nitro-2-(trifluoromethyl)-3-yl)benzonitrile | 300 | 0 | 0 | 0 | — |
| | 100 | — | — | — | — |
| | 50 | — | — | — | 8 |
| 2-(p-Chlorophenyl)-3-nitro-4-p-tolyl-5-(trifluoromethyl)-pyrrole | 300 | 5 | 0 | 0 | — |
| | 100 | 0 | 6 | 0 | — |
| | 50 | — | — | — | 0 |
| 2-(p-Chlorophenyl)-4-(o-chlorophenyl)-3-nitro-5-(trifluoromethyl)pyrrole | 300 | 5 | 0 | 0 | — |
| | 100 | 0 | 4 | 0 | — |
| | 50 | — | — | — | 0 |
| 2-(p-Chlorophenyl)-4-(p-methoxyphenyl)-3-nitro-5-(trifluoromethyl)pyrrole | 300 | 5 | 0 | 0 | — |
| | 100 | 0 | 5 | 0 | — |
| | 50 | — | — | — | 0 |
| 2-(p-Chlorophenyl)-4-(2,4-dichlorophenyl)-3-nitro-5-(trifluoromethyl)pyrrole | 300 | 0 | 0 | 0 | — |
| | 100 | — | 8 | 0 | — |
| | 50 | — | — | — | 0 |
| m-[5-(p-Chlorophenyl)-4-nitro-2-(trifluoromethyl)pyrrole-3-yl]benzonitrile | 300 | 0 | 0 | 0 | — |
| | 100 | — | — | — | — |
| | 50 | — | — | — | 7 |
| 2-(p-Chlorophenyl)-4-(3,4-difluorophenyl)-3-nitro-5- | 300 | 9 | 0 | 9 | — |
| | 100 | 9 | 9 | — | — |

TABLE II-continued

Evaluation of diaryl pyrrole carbonitriles and nitropyrroles as insecticidal and acaricidal agents

| Compound | Rate ppm | p-Resistant mites Adult | Egg | Nymph | Rootworm |
|---|---|---|---|---|---|
| (trifluoromethyl)pyrrole | 50 | — | — | — | 9 |

We claim:

1. A method for protecting living plants against attack by budworm, comprising, applying to said plants an insecticidally effective amount of a compound having the structure of formula I or II:

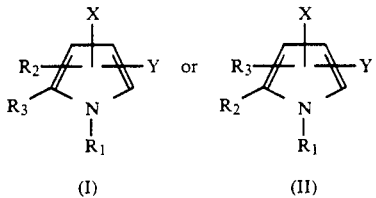

wherein
$R_1$ is H,
  $C_1$–$C_4$ alkyl or $C_2$–$C_4$ monohaloalkyl, each optionally substituted with from one to three additional halogen atoms, one cyano, one hydroxy, one unsubstituted benzoyl, one or two $C_1$–$C_4$ alkoxy groups each optionally substituted with one to three halogen atoms, one $C_1$–$C_4$ alkylthio, one $C_1$–$C_4$ carbalkoxy, one $C_1$–$C_6$ alkylcarbonyloxy, one $C_2$–$C_6$ alkenylcarbonyloxy, one benzenecarbonyloxy, or chloro, dichloro,.or methylsubstituted-benzenecarbonyloxy, one phenyl optionally substituted with $C_1$–$C_3$ alkoxy or with one to three halogen atoms, one phenoxy optionally substituted with one to three halogen atoms, or one benzyloxy optionally substituted with one halogen substituent;
  $C_3$–$C_4$ alkenyl optionally substituted with one to three halogen atoms;
  cyano;
  $C_3$–$C_4$ alkynyl optionally substituted with one halogen atom;
  di-($C_1$–$C_4$ alkyl)aminocarbonyl; or
  $C_3$–$C_6$ polymethyleneiminocarbonyl;
$R_2$ is CN or $NO_2$;
$R_3$ is $CF_3$;
X and Y are each independently phenyl optionally substituted with one or two halogen, CN, $NO_2$, $C_1$–$C_4$ alkyl, $C_1$–$C_4$ alkoxy, $CF_3$ or $OCF_2R_4$ groups; and
$R_4$ is H, F, $CHF_2$, $CHCl_2$ or $CF_3$.

2. The method according to claim 1 wherein the compound has the structure of formula I, $R_3$ is $CF_3$ and X and Y each represent a substituted phenyl group.

3. The method according to claim 1, wherein said compound is:
2,3-bis(p-chlorophenyl)-4-nitro-5-(trifluoromethyl)pyrrole;
2-(p-(chlorophenyl)-3-(3,4-dichlorophenyl)-4-nitro-5-(trifluoromethyl)pyrrole;
2-(p-chlorophenyl)-3-nitro-4-(m-nitrophenyl)-5-(trifluoromethyl)pyrrole;
2-(p-chlorophenyl)-4-(3,4-dichlorophenyl)-1-(ethoxymethyl)-3-nitro-5-(trifluoromethyl)pyrrole;
2-(p-chlorophenyl)-3-nitro-5-(trifluoromethyl)-4-(α,α,α-trifluoro-p-tolyl)pyrrole;
2-(p-chlorophenyl)-4-(3,4-dichlorophenyl)-3-nitro-5-(trifluoromethyl)pyrrole-1-carbonitrile;
3-(2-bromo-4,5-dimethoxyphenyl)-5-(p-chlorophenyl)-4-nitro-2-(trifluoromethyl)pyrrole;
2-(p-chlorophenyl)-4-(3,4-dichlorophenyl)-1-(1-ethoxymethyl)-3-nitro-5-(trifluoromethyl)pyrrole;
2-(p-chlorophenyl)-3-nitro-4-(p-nitrophenyl)-5-(trifluoromethyl)pyrrole;
2-(p-chlorophenyl)-4-(3,4-dichlorophenyl)-1-methyl-3-nitro-5-(trifluoromethyl)pyrrole;
2,3-bis(3,4-dichlorophenyl)-4-nitro-5-(trifluoromethyl)pyrrole;
2-(p-chlorophenyl)-3-nitro-4-phenyl-5-(trifluoromethyl)pyrrole;
2,4-bis(p-chlorophenyl)-3-nitro-5-(trifluoromethyl)pyrrole;
2-(p-chlorophenyl)-4-(3,4-dichlorophenyl)-3-nitro-5-(trifluoromethyl)pyrrole;
3-(p-chlorophenyl)-5-(3,4-dichlorophenyl)-4-nitro-2-(trifluoromethyl)pyrrole;
3-(p-chlorophenyl)-5-(3,4-dichlorophenyl)-1-(ethoxymethyl)-4-nitro-2-(trifluoromethyl)pyrrole;
2,4-bis(3,4-dichlorophenyl)-3-nitro-5-(trifluoromethyl)pyrrole;
3-(p-chlorophenyl-4-nitro-2-(trifluoromethyl)-5-(α,α,α-p-tolyl)pyrrole;
2-(p-chlorophenyl)-1-(ethoxymethyl)-3-nitro-5-(trifluoromethyl)-4-(α,α,α-trifluoro-p-tolyl)pyrrole;
p-[-5-(p-chlorophenyl)-4-nitro-2-(trifluoromethyl)pyrrol-3-yl]benzonitrile;
2-(p-chlorophenyl)-3-nitro-4-p-tolyl-5-(trifluoromethyl)pyrrole;
2-(p-chlorophenyl)-4-(p-chlorophenyl)-3-nitro-5-(trifluoromethyl)pyrrole;
2-(p-chlorophenyl)-4-(p-methoxyphenyl)-3-nitro-5-(trifluoromethyl)pyrrole;
2-bromo-3,5-bis(p-chlorophenyl)-4-nitropyrrole;
2-(p-chlorophenyl)-4-(2,4-dichlorophenyl)-3-nitro-5-(trifluoromethyl)pyrrole;
m-[5-(p-chlorophenyl)-4-nitro-2-(trifluoromethyl)pyrrol-3-yl]benzonitrile;
2-(p-chlorophenyl)-4-(2,6-dichlorophenyl)-3-nitro-5-(trifluoromethyl)pyrrole; or
2-(p-chlorophenyl)-4-(3,4-difluorophenyl)-3-nitro-5-(trifluoromethyl)pyrrole.

4. A method for controlling budworm comprising contacting said budworm with an insecticidally effective amount of a compound having the formula I or formula II structure:

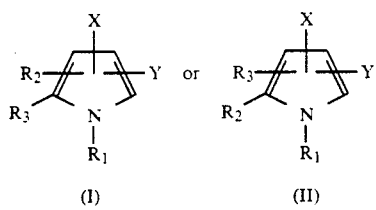

wherein
R₁ is H,
C$_1$-C$_4$ alkyl or C$_2$-C$_4$ monohaloalkyl, each optionally substituted with from one to three additional halogen atoms, one cyano, one hydroxy, one unsubstituted benzoyl, one or two C$_1$-C$_4$ alkoxy groups each optionally substituted with one to three halogen atoms, one C$_1$-C$_4$ alkylthio, one C$_1$-C$_4$ carbalkoxy, one C$_1$-C$_6$ alkylcarbonyloxy, one C$_2$-C$_6$ alkenylcarbonyloxy, one benzenecarbonyloxy, or chloro, dichloro, or methylsubstituted-benzenecarbonyloxy, one phenyl optionally substituted with C$_1$-C$_3$ alkoxy or with one to three halogen atoms, one phenoxy optionally substituted with one to three halogen atoms, or one benzyloxy optionally substituted with one halogen substituent;
C$_3$-C$_4$ alkenyl optionally substituted with one to three halogen atoms;
cyano;
C$_3$-C$_4$ alkenyl optionally substituted with one halogen atom;
di-(C$_1$-C$_4$ alkyl)aminocarbonyl; or
C$_3$-C$_6$ polymethyleneiminocarbonyl;
R$_2$ is CN or NO$_2$;
R$_3$ is halogen or CF$_3$;
X and Y are each independently phenyl optionally substituted with one or two halogen, CN, NO$_2$, C$_1$-C$_4$ alkyl, C$_1$-C$_4$ alkoxy, CF$_3$ or OCF$_2$R$_4$ groups; and
R$_4$ is H, F, CHF$_2$, CHCl$_2$ or CF$_3$.

5. The method according to claim 4 wherein said compound is a formula I compound, applied at the rate of from 0.16 kg/ha to 4.0 kg/ha, to plant foliage in the feeding grounds of said budworm, the habitat of said budworm or their breeding ground.

6. The method according to claim 4 wherein said formula I or formula II compound is applied to the feed supply of said budworm, their habitat or their breeding grounds as an aqueous spray containing from 10 ppm to 10,000 ppm of said formula I or formula II compound.

7. The method according to claim 4 wherein said compound is:

2,3-bis(p-chlorophenyl)-4-nitro-5-(trifluoromethyl)pyrrole;
2-(p-(chlorophenyl)-3-(3,4-dichlorophenyl)-4-nitro-5-(trifluoromethyl)pyrrole;
2-(p-chlorophenyl)-3-nitro-4-(m-nitrophenyl)-5-(trifluoromethyl)pyrrole;
2-(p-chlorophenyl)-4-(3,4-dichlorophenyl)-1-(ethoxymethyl)-3-nitro-5-(trifluoromethyl)pyrrole;
2-(p-chlorophenyl)-3-nitro-5-(trifluoromethyl)-4-(α,α,α-trifluoro-p-tolyl)pyrrole;
2-(p-chlorophenyl)-4-(3,4-dichlorophenyl)-3-nitro-5-(trifluoromethyl)pyrrole-1-carbonitrile;
3-(2-bromo-4,5-dimethoxyphenyl)-5-(p-chlorophenyl)-4-nitro-2-(trifluoromethyl)pyrrole;
2-(p-chlorophenyl)-4-(3,4-dichlorophenyl)-1-(1-ethoxymethyl)-3-nitro-5-(trifluoromethyl)pyrrole;
2-(p-chlorophenyl)-3-nitro-4-(p-nitrophenyl)-5-(trifluoromethyl)pyrrole;
2-(p-chlorophenyl)-4-(3,4-dichlorophenyl)-1-methyl-3-nitro-5-(trifluoromethyl)pyrrole;
2,3-bis(3,4-dichlorophenyl)-4-nitro-5-(trifluoromethyl)pyrrole;
2-(p-chlorophenyl)-3-nitro-4-phenyl-5-(trifluoromethyl)pyrrole;
2,4-bis(p-chlorophenyl)-3-nitro-5-(trifluoromethyl)pyrrole;
2-(p-chlorophenyl)-4-(3,4-dichlorophenyl)-3-nitro-5-(trifluoromethyl)pyrrole;
3-(p-chlorophenyl)-5-(3,4-dichlorophenyl)-4-nitro-2-(trifluoromethyl)pyrrole;
3-(p-chlorophenyl)-5-(3,4-dichlorophenyl)-1-(ethoxymethyl)-4-nitro-2-(trifluoromethyl)pyrrole;
2,4-bis(3,4-dichlorophenyl)-3-nitro-5-(trifluoromethyl)pyrrole;
3-(p-chlorophenyl)-4-nitro-2-(trifluoromethyl)-5-(α,α,α-p-tolyl)pyrrole;
2-(p-chlorophenyl)-1-(ethoxymethyl)-3-nitro-5-(trifluoromethyl)-4-(α,α,α-trifluoro-p-tolyl)pyrrole;
p-[-5-(p-chlorophenyl)-4-nitro-2-(trifluoromethyl)pyrrol-3-yl]benzonitrile;
2-(p-chlorophenyl)-3-nitro-4-p-tolyl-5-(trifluoromethyl)pyrrole;
2-(p-chlorophenyl)-4-(o-chlorophenyl)-3-nitro-5-(trifluoromethyl)pyrrole;
2-(p-chlorophenyl)-4-(p-methoxyphenyl)-3-nitro-5-(trifluoromethyl)pyrrole;
2-bromo-3,5-bis(p-chlorophenyl)-4-nitropyrrole;
2-(p-chlorophenyl)-4-(2,4-dichlorophenyl)-3-nitro-5-(trifluoromethyl)pyrrole;
m-[5-(p-chlorophenyl)-4-nitro-2-(trifluoromethyl)pyrrol-3-yl]benzonitrile;
2-(p-chlorophenyl)-4-(2,6-dichlorophenyl)-3-nitro-5-(trifluoromethyl)pyrrole; or
2-(p-chlorophenyl)-4-(3,4-difluorophenyl)-3-nitro-5-(trifluoromethyl)pyrrole.

* * * * *